(12) United States Patent
Jonkers

(10) Patent No.: US 6,734,027 B2
(45) Date of Patent: May 11, 2004

(54) INSPECTION SYSTEM FOR PROCESS DEVICES FOR TREATING SUBSTRATES, SENSOR INTENDED FOR SUCH INSPECTION SYSTEM, AND METHOD FOR INSPECTING PROCESS DEVICES

(75) Inventor: Otto Cornelius Jonkers, Soest (NL)

(73) Assignee: ASM International, N.V., BC Bilthoven (NL)

( * ) Notice: Subject to any disclaimer, the term of this patent is extended or adjusted under 35 U.S.C. 154(b) by 57 days.

(21) Appl. No.: 10/099,870

(22) Filed: Mar. 14, 2002

(65) Prior Publication Data

US 2002/0148307 A1 Oct. 17, 2002

(30) Foreign Application Priority Data

Mar. 14, 2001 (NL) .............................................. 1017593

(51) Int. Cl.[7] .............................................. H01L 21/66
(52) U.S. Cl. ........................... 438/14; 438/16; 73/865.9
(58) Field of Search .................... 438/14, 16; 73/865.8, 73/865.9; 700/112, 113, 121

(56) References Cited

U.S. PATENT DOCUMENTS

| 4,543,576 | A | | 9/1985 | Hieber et al. .......... 340/870.17 |
|---|---|---|---|---|
| 5,213,985 | A | * | 5/1993 | Sandroff et al. ................ 438/7 |
| 5,233,191 | A | | 8/1993 | Noguchi et al. ............ 250/306 |
| 5,444,637 | A | | 8/1995 | Smesny et al. ............. 364/556 |
| 6,069,588 | A | | 5/2000 | O'Neill ....................... 343/713 |
| 6,073,501 | A | | 6/2000 | Rohner ....................... 73/865.8 |
| 6,111,248 | A | * | 8/2000 | Melendez et al. .......... 250/239 |
| 6,174,205 | B1 | * | 1/2001 | Madsen et al. ............. 439/638 |
| 6,244,121 | B1 | * | 6/2001 | Hunter ....................... 73/865.9 |
| 6,352,466 | B1 | * | 3/2002 | Moore ............................ 451/5 |
| 6,499,367 | B1 | * | 12/2002 | Saeki ........................ 73/865.9 |

* cited by examiner

Primary Examiner—Matthew Smith
Assistant Examiner—Lex H. Malsawma
(74) Attorney, Agent, or Firm—Weingarten, Schurgin, Gagnebin & Lebovici LLP

(57) ABSTRACT

The invention relates to an inspection system for process equipment for treating substrates, such as, for instance, semiconductor wafers or flat panel displays. The system is provided with a wireless sensor with which the interior of the process device can be inspected. The sensor is provided with a transmitter to transfer a signal, during inspection of the interior of the process device, to a receiver disposed outside the process device. The wireless sensor is arranged on a support having substantially the same dimensions as the substrates to be treated.

15 Claims, 4 Drawing Sheets ized cassettes. According-
INSPECTION SYSTEM FOR PROCESS DEVICES FOR TREATING SUBSTRATES, SENSOR INTENDED FOR SUCH INSPECTION SYSTEM, AND METHOD FOR INSPECTING PROCESS DEVICES

FIELD OF THE INVENTION

This invention relates to an inspection system for process equipment for treating substrates, such as, for instance, semiconductor wafers or flat panel displays.

BACKGROUND OF THE INVENTION

During the performance of a process treatment on substrates such as semiconductor wafers or flat panel displays, a strict control of the process parameters is required. Therefore process treatment typically takes place in a process chamber which is closed to the surroundings. Such a process chamber can be a vacuum chamber. To ensure a controlled process, the process chamber is provided with fixedly arranged sensors, for instance for measuring the temperature and the pressure. These sensors can be arranged in the chamber itself but it is also possible that the sensors are arranged outside the chamber and measure via a window provided in the wall of the chamber. When sensors are fixedly arranged in the process chamber, the sensors must be resistant to the process conditions used. This imposes a limitation on what sensors can be used for this purpose. The arrangement of sensors outside the process chamber and measuring through a window likewise imposes limitations on what sensors can be used and what quantities can be measured with them. In some processes, such as those where a thin layer is deposited on the substrates, the equipment is subject to fouling and regular servicing is required. It is then important that such maintenance be performed at the right time: not too soon, which would lead to unnecessarily high costs and to reduced availability of the equipment, nor too late, which would lead to poor process results and product rejection. The possibility of visually inspecting the interior of the process chamber would lead to a better determination of the moment of maintenance. A camera permanently arranged in the process chamber is naturally subject to the same fouling as the process chamber itself and the question is if a proper observation could be made with it. In addition, the question is if such a camera would survive the process conditions of elevated temperature, reactive gases, vacuum and the like. Also, in special circumstances, there may be a need to measure parameters in the process chamber such as temperature, pressure, gas concentration, ionization degree of the gas, and the like, this in addition to, or for comparison with, the information supplied by the fixedly arranged sensors. Normally, it is not possible to perform such additional measurements without making the process chamber accessible for inspection through disassembly. Another need for an inspection possibility occurs in programming the substrate transport mechanism which transports the substrates in such process equipment from an input station to the process chamber and back again. The substrate must then be accurately deposited in the correct position in the process chamber. During programming, visual control is a requirement. This means that the programming of the substrate transport mechanism must take place with the chamber disassembled. As an alternative, the visual control can take place through the window. The question is, however, how accurately a visual control can be done through a window, in view of light diffraction.

SUMMARY OF THE INVENTION

The object of the present invention is to provide a solution to the above problems and to provide an inspection system with which at any time the interior of the process chamber can be inspected, or with which measurements in the interior of the process chamber can be carried out without the necessity of dismounting the process chamber.

This object is achieved in that the inspection system comprises a sensor which is provided with a transmitter for wireless communication and a receiver disposed outside the process device, while the sensor provided with a transmitter is arranged on a support having substantially the same shape and dimensions as the substrates to be treated.

When the process device is provided with a transport mechanism for transporting the substrates, the support with the wireless sensor arranged thereon can be transported from outside the process chamber to the interior of the process chamber and vice versa in the same manner as the substrates to be treated.

The invention also relates to a sensor provided with a transmitter for wireless communication, for inspecting the interior of a process device for treating substrates, the sensor being arranged on a support having substantially the same shape and dimensions as the substrates to be treated. Such a sensor can be applied fruitfully in an inspection system according to the invention.

The invention further relates to a method for inspecting the interior of a process device for treating substrates, wherein the process device is provided with an input/output station for the input/output of substrates, at least one process chamber for treating substrates and substrate transport means for transporting the substrates from the input/output station to the process chamber and vice versa, wherein a sensor provided with a transmitter is placed on the input/output station and is transported with the substrate transport means to the interior of the process device for performing the inspection, wherein during the inspection the transmitter transmits a signal which can be received with a receiver disposed outside the process device, and wherein after completion of the inspection the sensor is placed on the input/output station again with the substrate transport means.

With such a method, the interior of a process chamber of the process equipment can be inspected in a highly efficient manner. Moreover, the operation of the substrate transport means can be inspected during use without the housing or the like needing to be removed.

According to a further elaboration of the invention, the method is characterized in that programming of the substrate transport mechanism takes place during the visual inspection, on the ground of the information supplied by the camera. Further, according to a further elaboration of the method according to the invention, adjustment of the process device can take place during inspection, on the ground of the information supplied by the sensor.

DETAILED DESCRIPTION OF THE INVENTION

In a process device for machined treatment of substrates, the substrates are supplied while placed in cassettes. According to the invention, on such a substrate, a wireless sensor is fitted. Instead of a standard substrate, also a special sensor support can be used, such that the external dimensions are substantially equal to those of a standard substrate, so that the sensor support can be carried to the process chamber by the substrate transport mechanism and that the sensor support fits in a substrate position in the process chamber. For the sensor support, instead of the usual substrate material, a different material can be chosen, for instance aluminum, or another metal or an alloy or glass. On the upper side of the support, the sensor can be provided. An example of such a sensor is the video telemetry capsule endoscope as described in Gavriel Iddan et al. in Nature, Vol. 405, May 2000, p. 417. This camera capsule has no external connections by means of wires, glass fiber cables or other physical connections. The dimensions are 11×30 mm. The capsule is provided with a battery and a transmitter which transmits in the UHF range. The UHF signal is received by one or more antennas connected with a receiver. The receiver can be connected with a storage system for storing the received images or with a Video imaging system for reproducing the images or with a computer. A telemetric system for the wireless transfer of the signal utilizes, according to the prior art, a pulse code modulation (PCM) method. The above-described camera capsule is used for inspecting the stomach wall of a patient. To that end, the patient swallows the capsule and the UHF signal transmitted by the capsule is received with antennas fitted on the body. In due course, the capsule leaves the body by the usual route via the gastrointestinal tract. In this way, such an inspection can be carried out without requiring surgical intervention.

When such a sensor fitted on a support is used in the interior of a process device, the antenna can be disposed outside the process device. Depending on the thickness and nature of the material of the walls of the process device, however, it may be necessary for a proper reception to dispose the antenna in the interior of the process device, while the signal is brought outside by means of a signal line and a lead-through.

For the wireless transfer of the signal, instead of the more conventional radio techniques, the world standard "Bluetooth" technology can be utilized. The Bluetooth technology utilizes a radio signal in the frequency band of 2.4 to 2.48 GHz, applies a spread spectrum, frequency jumping and a complete duplex signal with 1600 frequency jumps per second. The signal jumps between 79 frequencies located at a mutual interval distance of 1 MHz to achieve a high degree of interference immunity. This technology is especially suitable for signal transfer over a short distance, 10 m, and is optionally suitable for signal transfer over a medium-range distance, 100 m. An example of an application is given in U.S. Pat. No. 6,069,588 in the name of O'Neill. The advantage of a transmission system according to the Bluetooth technology is that the chips required therefor are particularly compact and energetically economic. Moreover, since this technique focuses on consumer applications, the costs of these chips will be low.

As a further alternative to wireless transfer, use can also be made of infrared signal techniques, for instance according to the standard IrDA, known to those skilled in the art. The disadvantage of infrared techniques, however, is that a line of sight is necessary, penetrable for infrared light.

In addition to the example of a camera mentioned, many other sensors are conceivable. For instance sensors for temperature, pressure, concentration of gas, ionization degree of a gas, acceleration and other quantities. The use of the same technique for manufacturing sensors as for manufacturing integrated electronic circuits leads to the situation that many compact and energetically economical sensors are available and are becoming available. These sensors are in particular suitable for use according to the invention.

What has been contemplated for the application of the invention is, in particular, process equipment for treating silicon wafers. Such wafers are costly and a proper control of the process equipment is of eminent importance. This applies in particular to wafers having a large diameter, for instance 200 mm, or the largest wafer currently in use, 300 mm. The sensor can be provided on a wafer, together with a transmitter and an energy supply. The energy supply can consist of a battery. To be considered as an alternative is a solar cell, in which case the process device must provide for irradiation with light. When the substrate is a silicon wafer, the sensor and/or the transmitter can also be provided in, instead of on, the wafer, by means of the technique for manufacturing electronic circuits.

It is noted that U.S. Pat. No. 4,543,576 discloses a wireless measuring system which, in a vapor deposition system, during vapor deposition, measures the temperature and resistance of the vapor deposited layer on a reference substrate, while outside the vapor deposition chamber a receiver is disposed. In this vapor deposition system, the measuring system is mounted on a movable substrate holder which during vapor deposition is moved to improve the uniformity of the vapor deposited layer. However, the measuring system described in this U.S. patent specification is large compared with the substrate and is connected with the position of the reference wafer. In the above U.S. patent specification, it is not described that the substrate itself can serve as a support of the sensor, so that the substrate provided with a sensor can be transported with the substrate transport mechanism through the process device to any substrate position in the system. Moreover, in this known apparatus, it is not the process equipment itself that is inspected, but the layer which is formed with this equipment.

BRIEF DESCRIPTION OF THE FIGURES

Further elaborations of the invention are described in the subclaims and will hereinafter be further clarified on the basis of a number of exemplary embodiments with reference to the description of the drawings.

FIG. 1 schematically represents an inspection system according to the invention. The sensor is designated by 2, a signal processing unit by 3 and the transmitter by 4. These three modules are supplied by the energy supply 5 with which they are jointly arranged on the substrate. The whole is disposed in process device 1. Arranged outside the device is antenna 6, this antenna being connected with receiver 9 and with computer 10. Instead of a computer, also a device for reproducing and/or storing video images can be utilized.

In FIG. 2, another embodiment of an inspection system according to the invention is shown. Identical reference numerals indicate identical components to those in FIG. 1. In FIG. 2, the antenna is disposed in the interior of the process device and connected with receiver 9 via lead-through 7 and signal line 8.

FIG. 3 shows a side elevation of a substrate 20 having thereon the camera capsule 21 mentioned earlier. As a substrate, a 300 mm silicon wafer has been taken, and the camera having a diameter of 11 mm and a length of 30 mm is indicated on scale thereon. FIG. 4 shows a top plan view of a wafer having arranged thereon a camera capsule. Depending on the situation in which the sensor wafer is used and the need for inspection, several cameras can be arranged on the wafer, as shown in FIG. 5. Optionally, two cameras arranged parallel and substantially at eye distance can be used, so that a stereo image can be created. In addition, it is possible for the cameras to be arranged displaceably on the wafers, with the aid of any technique known for that purpose, such as clamping, adhesion, magnets, and the like. Depending on the space in the process device and the transport mechanism for the substrate, the camera can also be attached to the undersurface of the wafer. Finally, it is also possible to provide a recess in the support and to have the camera project partly above the wafer and partly under the wafer.

The invention provides the possibility, when using the camera capsule, to program the substrate transport mechanism and to observe the result of changes in programming immediately. Such programming can therefore be done interactively, so that a substrate is accurately placed in the desired position by the substrate transport mechanism. When using other sensors, other quantities of the process device can be adjusted, such as, for instance, the pressure, or the center of a pressure sensor fixedly arranged in the process device, or the mechanical alignment of the process device. In general, the invention provides the possibility of performing adjustments on the process device during inspection, on the ground of the information supplied by the sensor.

Figure 1:
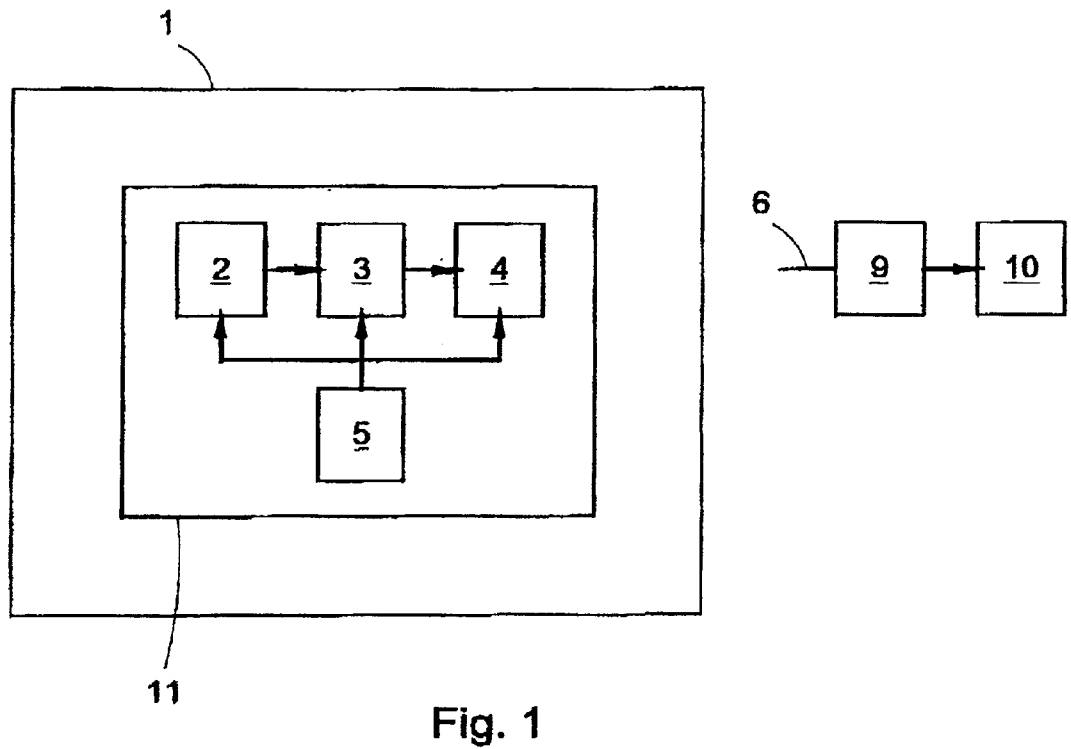
FIG. 1 is a schematic representation of a first embodiment of an inspection system.
Figure 2:
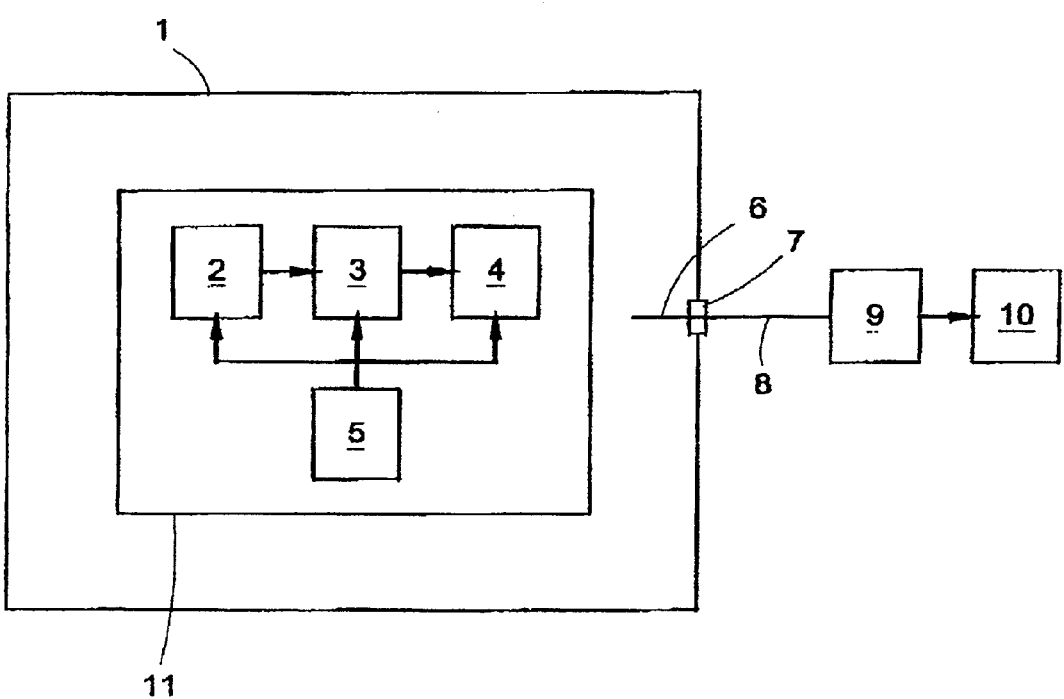
FIG. 2 is a schematic representation of a second embodiment of an inspection system.
Figure 3:
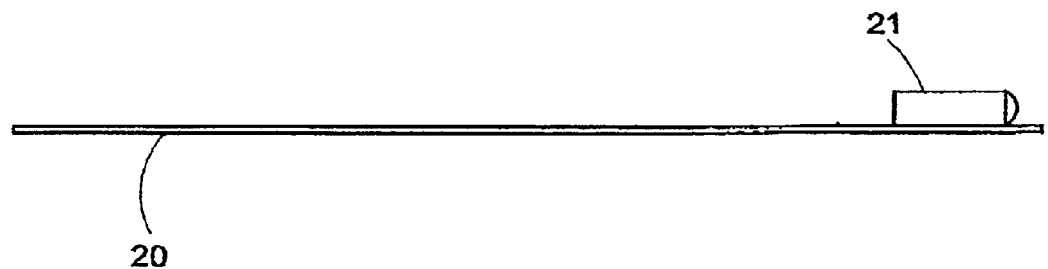
FIG. 3 is a side elevation of a substrate with a camera capsule provided thereon.
Figure 4:
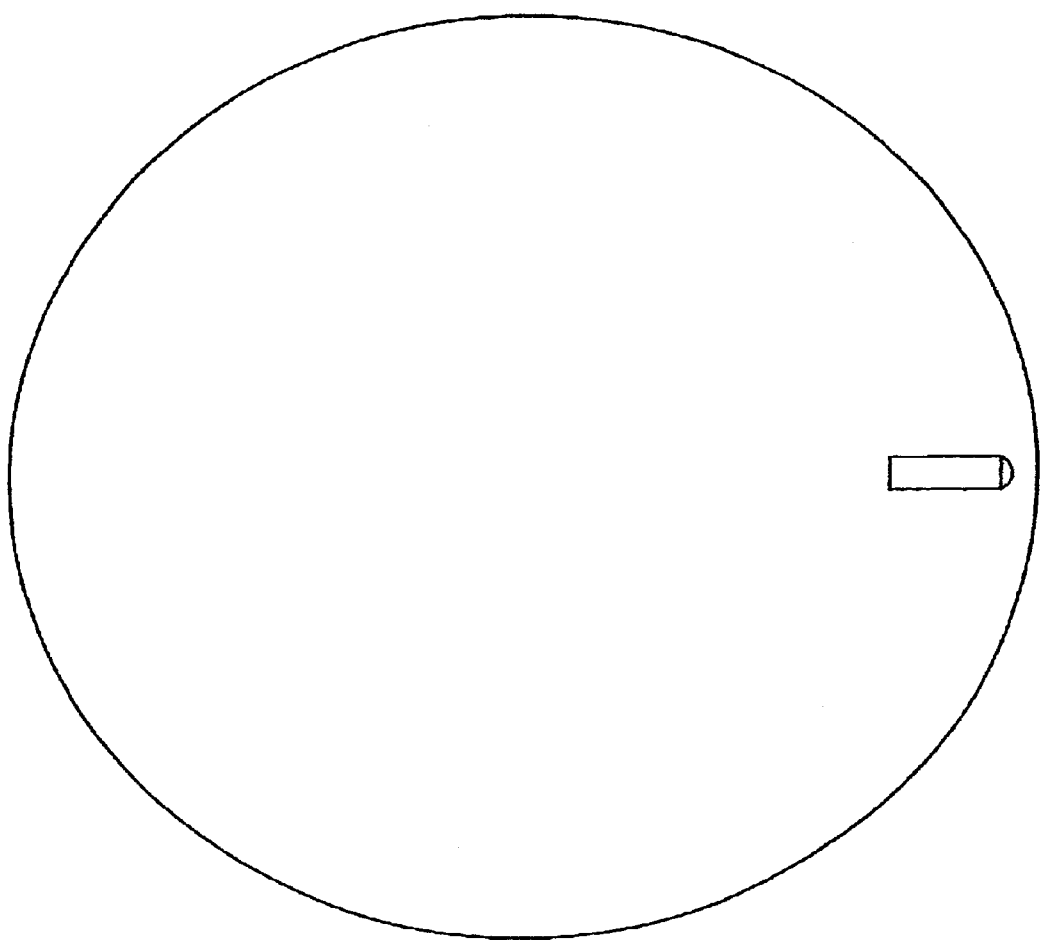
FIG. 4 is a top plan view of a substrate having a camera capsule provided thereon.
Figure 5:
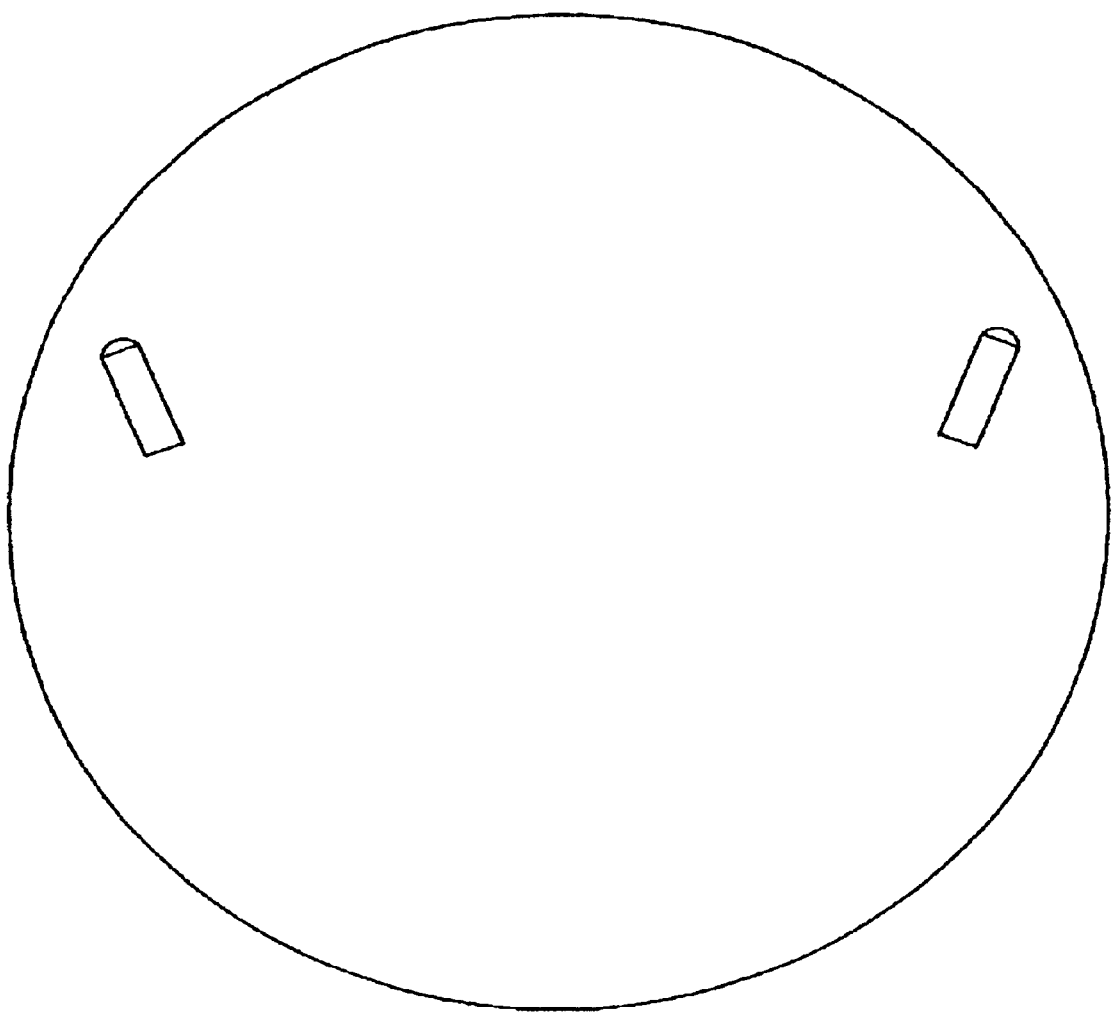
FIG. 5 is a top plan view of a substrate having two camera capsules provided thereon.
Figure 6:
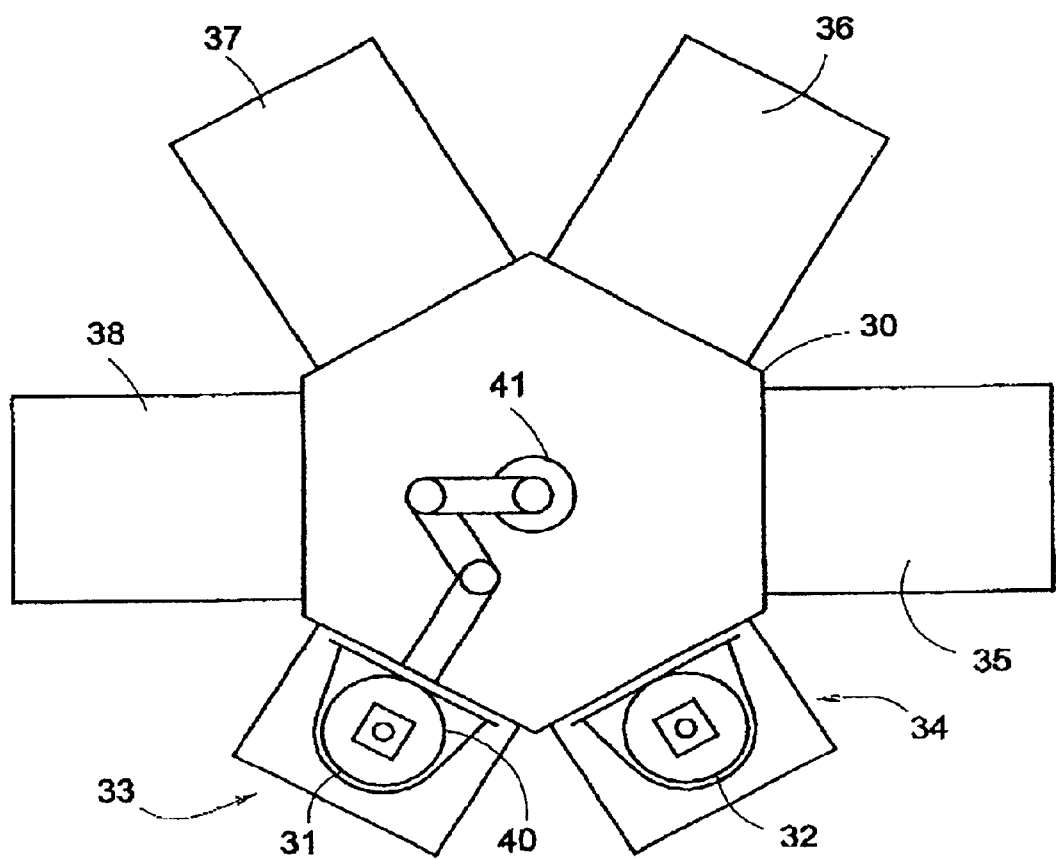
FIG. 6 is a schematic representation of a process device for treating substrates.

In FIG. 6, an example of a process device for treating substrates is represented. Treatment chambers 35, 36, 37 and 38 are connected with a central substrate transport chamber 30. The substrates 40 are supplied in cassettes 31 and 32 via input stations 33 and 34. The substrate transport mechanism 41 transports the substrates from the cassettes 31, 32 to one of the treatment chambers for treating the substrate. It is conventional to treat the substrates one by one in a treatment chamber. It is also possible, however, to treat a number of substrates simultaneously in a treatment chamber.

What is claimed is:

1. An inspection system for process equipment for treating substrates, semiconductor wafers or flat panel displays, the system being provided with a wireless sensor with which the interior of the process device can be inspected, the sensor being provided with a transmitter to transfer a signal, during inspection of the interior of the process device, to a receiver located outside the process device, the wireless sensor being arranged on a support having substantially the same dimensions as the substrates to be treated, wherein the sensor includes a micro video camera.

2. An inspection system according to claim 1, wherein, for the purpose of a process device provided with substrate transport means, the wireless sensor is arranged on the support, such that the support can be transported in the process device with said substrate transport means.

3. An inspection system according to claim 2, wherein for the wireless communication an infrared technique is used.

4. An inspection system according to claim 2, wherein for the wireless communication a radio technique is used.

5. An inspection system according to claim 1, wherein for the wireless communication an infrared technique is used.

6. An inspection system according to claim 1, wherein for the wireless communication a radio technique is used.

7. An inspection system according to claim 6, wherein an antenna for receiving the signal transmitted by the wireless sensor is disposed outside the process device.

8. An inspection system according to claim 6, wherein an antenna for receiving the signal transmitted by the wireless sensor is disposed in the interior of the process device.

9. An inspection system according to claim 6, wherein for the wireless communication the "Bluetooth" technology is used.

10. A sensor provided with a transmitter for wireless communication, for inspecting the interior of a process device for treating substrates, the sensor being arranged on a support having substantially the same shape and dimensions as the substrates to be treated, wherein the sensor includes a micro video camera.

11. A sensor according to claim 10, wherein the sensor is arranged on a silicon wafer.

12. A sensor according to claim 10, wherein the support is provided with two sensors designed as micro video cameras, arranged substantially parallel and at eye distance front each other, so that a stereo image can thereby be obtained.

13. A method for inspecting the interior of a process device for treating substrates, wherein the process device is provided with an input/output station for the input/output of substrates, at least one process chamber for treating substrates and substrate transport means to transport the substrates from the input/output station to the process chamber and vice versa, wherein a sensor provided with a transmitter is placed on the input/output station and is transported with the substrate transport means to the interior of the process device for performing the inspection, wherein during the inspection the transmitter transmits a signal which can be received with a receiver disposed outside the process device, and wherein after completion of the inspection the sensor is placed on the input/output station again with the substrate transport means, wherein the sensor is a camera and the inspection is a visual inspection.

14. A method according to claim 13, wherein programming of the substrate transport mechanism takes place during the visual inspection on the ground of the information supplied by the camera.

15. A method according to claim 13, wherein adjustment of the process device takes place during inspection on the ground of the information supplied by the sensor.

* * * * *

UNITED STATES PATENT AND TRADEMARK OFFICE
CERTIFICATE OF CORRECTION

PATENT NO. : 6,734,027 B2
DATED : May 11, 2004
INVENTOR(S) : Otto Cornelius Jonkers It is certified that error appears in the above-identified patent and that said Letters Patent is hereby corrected as shown below:

Column 5,
Line 3, "substrate," should read -- substrate 20, --.

Signed and Sealed this

Nineteenth Day of April, 2005

JON W. DUDAS
*Director of the United States Patent and Trademark Office*